United States Patent [19]

Cosyns et al.

[11] 3,966,833

[45] June 29, 1976

[54] PROCESS FOR HYDRODEALKYLATING ALKYLAROMATIC HYDROCARBONS

[75] Inventors: Jean Cosyns, Nanterre; Bernard Juguin; Jean-François Le Page, both of Rueil-Malmaison; Jean Miquel, Paris, all of France

[73] Assignee: Institut Francaise du Petrole, Rueil-Malmaison, France

[22] Filed: Dec. 13, 1974

[21] Appl. No.: 532,618

[30] Foreign Application Priority Data

Dec. 13, 1973 France.............................. 73.44690

[52] U.S. Cl............................ 260/672 R; 208/135; 208/136; 208/138
[51] Int. Cl.$^2$........................................... C07C 3/58
[58] Field of Search................. 260/672 R; 208/135, 208/136, 138

[56] References Cited
UNITED STATES PATENTS

| | | |
|---|---|---|
| 2,838,444 | 6/1958 | Teter et al. ......................... 208/138 |
| 3,291,850 | 12/1966 | Carson ............................... 260/672 |
| 3,306,944 | 2/1967 | Pollitzer ............................. 260/672 |
| 3,595,932 | 7/1971 | Maslyansky et al. ............... 260/672 |
| 3,649,707 | 3/1972 | Lester ................................ 260/672 |
| 3,833,516 | 9/1974 | Sawyer .............................. 208/136 |
| 3,857,780 | 12/1974 | Gustafson .......................... 208/135 |

*Primary Examiner*—Delbert E. Gantz
*Assistant Examiner*—C. E. Spresser
*Attorney, Agent, or Firm*—Millen, Raptes & White

[57] ABSTRACT

Process for hydrodealkylating an alkylaromatic hydrocarbon charge at a temperature from 400° to 650°C under a pressure from 1 to 30 kg/cm$^2$ at a space velocity from 1 to 10 by reacting said charge with hydrogen in a molar proportion with respect to the effluent of the reactor in the range from 1 to 10, in the presence of a catalyst containing alumina and at least one metal selected from ruthenium, osmium, palladium, rhodium, iridium, platinum and manganese in an amount from 0.05 to 5 % of the catalyst, said catalyst having a specific surface from 1 to 100 m$^2$/g., a total pore volume of 0.2-0.8 g/cc and a heat of neutralization lower than 10 calories per gram are measured by ammonia adsorption at 320° C. under 300 mm Hg.

11 Claims, No Drawings

PROCESS FOR HYDRODEALKYLATING ALKYLAROMATIC HYDROCARBONS

This invention concerns a new process for the catalytic hydrodealkylation of alkyl aromatic hydrocarbons to benzene. The alkyl aromatic hydrocarbons comprise toluene or different xylenes or any alkyl aromatic hydrocarbon having 9 or more carbon atoms per molecule or an alkyl naphthalene hydrocarbon, etc... The feed charge subjected to hydrodealkylation contains either one of the above-mentioned hydrocarbons in a pure state or mixtures of those hydrocarbons, in the optional presence of various other hydrocarbons, for example, in the presence of paraffins. The cuts containing aromatic hydrocarbons subjected to hydrodealkylation are generally obtained from various sources as the effluents from reforming units and from various pyrolysis processes such as, for example, steam cracking. The aromatic cuts used as feed charge subjected to hydrodealkylation and which are produced from the above-mentioned sources, may have been subjected to various treatments of purification by distillation and extraction as well as to treatments for increasing their total aromatic content and, correspondingly, decreasing their naphthene and paraffin content. These latter treatments (sometimes called "aromizing") have been described in detail, for example in the French patent of addition number 2 170 899 and the German patent application No. 2400452. The cuts subjected to hydrodealkylation might also have been treated for the purpose of removing certain constituents such as sulfur, nitrogen, various metals and so on...

One feature of the prior art is that the process must be conducted, in practice, under very severe conditions of temperature and pressure as well as very low space velocities which make the use of these processes difficult and very costly. Thus, for example, in the thermal processes, it is necessary, in order to obtain substantial yields, to operate at temperatures of at least 700°C and under pressures of at least 40 kg/cm$^2$ and with space velocities which do not exceed 1. The catalytic processes must generally make use of catalysts based, for example, on chromium or molybdenum oxides, working under similar conditions of pressure and space velocity and at temperatures which do not substantially below 700°C. Another disadvantage of these processes is the formation, as byproducts, of very heavy aromatic hydrocarbons, precursors of coke, which clog the catalyst and the reactor and are detrimental to the yield of the operation. The process of the invention may be conducted under very favorable operating conditions which are as follows: temperature from 400° to 650°C and preferably from 500° to 620°C, pressure from 1 to 30 kg/cm$^2$ and preferably, from 1 to 20 kg/cm$^2$ and space velocities from 1 to 10 and preferably from 2 to 8.

The process of the invention, which may be conducted under favorable operating conditions and which gives good results is characterized in that the alkylaromatic feed is contacted in the preceding conditions with hydrogen in a reaction zone in the presence of a catalyst containing essentially:

a. at least one metal selected from the group consisting of the noble metals from group VIII of the periodic classification of elements and manganese, and
b. alumina, the specific surface of the catalyst being from 1 to 100 m$^2$/g, preferably from 5 to 80 m$^2$/g, more particularly from 7 to 55 m$^2$/g and more specifically from 10 to 45 m$^2$/g; preferably the total pore volume of the catalyst is from 0.2 to 0.8 cc/g, preferably from 0.3 to 0.7 cc/g, 75 % at least of the porosity corresponding to pores of an average diameter in the range from 100 to 150 angstroems; the heat of neutralization of the catalyst by ammonia adsorption is preferably less than 10 calories and more specifically less than 7 calories per gram of catalyst at 320°C under a pressure of 300 mm Hg. Accordingly, the acidity of the carrier must be low.

The acidity of the catalyst may be determined by the known test of ammonia adsorption, such as described, for example, in "Journal of Catalysis" 2,211–222 (1963): this method consists of heating the catalyst to 600°C under vacuum (i.e. at a pressure lower than about 0.01 mm Hg) to achieve complete gas removal (in order particularly to remove the water and the undesirable impurities); then the catalyst is placed in a calorimeter at 320°C, ammonia is introduced in such an amount that the final pressure of the system at the equilibrium reaches 300 mm Hg and the amount of heat evolved is measured. It is noticeable that the neutralization heat of the alumina used as carrier of the hydrodealkylation catalyst is substantially identical to that of the catalyst itself and that also the specific surface and the pore volume of the alumina used as carrier are substantially identical to the values given above for the catalyst itself.

It has been observed that among the catalysts having the same metal composition, the best activities and selectivities in the reaction conditions are obtained by those which have the above-mentioned specific surface, pore volume and neutralization heat.

The alumina used as carrier might also be characterized by its inertia with respect to the cracking and coking reactions in the presence of hydrogen. This characterization may be performed in any convenient manner. By way of example of test, we may use the cracking of a molecule easy to crack such as n-heptane which may be cracked at temperatures considerably lower than the temperature required for cracking the alkylaromatic hydrocarbons. Alumina will be considered as inert if, at 500°C, the n-heptane injected, at a space velocity of 1, on the carrier in fixed bed placed in a reactor under a hydrogen pressure of 20 bars and at a flow rate thereof equal to 4 moles per mole of charged n-heptane, is recovered at the outlet of the reactor in an amount of at least 99% by weight of the injected amount.

Among the aluminas which can be used as a carrier, the gamma alumina balls are particularly convenient. It is also possible to make use of other alumina conglomerates such as extrudates or pills having the required specific surface, pore volume acidity.

The noble metals of group VIII are ruthenium, osmium, palladium, rhodium, iridium and platinum.

In view of their activity, selectivity and particularly their stability, it may be preferable to make use of metal couples such as platinum-iridium, platinum-ruthenium, iridium-ruthenium, rhodium-manganese, platinum-manganese, platinum-rhodium and platinum-osmium.

The catalyst may also contain a group VIII metal (such as ruthenium, osmium, palladium, rhodium, iridium and platinum) or manganese, the selected metal being used in conjunction with another metal which is known as useful for hydrodealkylation, selected for example from nickel, molybdenum, tungsten and rhenium. We can mention such couples as platinum-tungsten, iridium-tungsten, ruthenium-tungsten, iridium-rhenium, ruthenium-rhenium, planium-rhenium, platinum-molybdenum, manganese-tungsten and manganese-molybdenum.

The metal content by weight of the catalyst (or the content of each of the metals when the catalyst contains several metals) will be from 0.05 to 5% and preferably from 0.1 to 1%. When the catalyst contains couples of metals, the atomic ratio of the metals of said couple may be, for example, from 0.1 to 20.

For example, or a catalyst havng a total metal content of 1%, the content in one of said two metals may be from 0.1 to 0.9 % while the content of the other metal will vary complementarily.

The method of manufacture of the catalysts is not a critical feature of the invention and any known method can be used. The active elements will be, for example, deposited (separately or preferably simultaneously in the case of use of a couple of metals) on the carrier through impregnation by solutions containing the same, for example aqueous solutions of manganese nitrate, platinum, iridium, rhodium or ruthenium chloride, osmic acid, hexachloroplatinic, hexachloroiridic or chlorosmic acid. The metals known for use in hydrodealkylation when combined with a metal from group VIII or with manganese are deposited on the carrier by means of solutions such as the noble hexachlorometallates of tungstate, molybdate, ammonium perrhenate, etc... This list is not limitative and any other salt or organo metallic compound soluble in water or in an organic solvent may also be used.

Once the metal elements have been deposited on the carrier, the catalyst is then dried, roasted by heating in an oxidizing, reducing or inert atmosphere according to the case, at a temperature of, for example, from 300° to 600°C, and then reduced in a hydrogen stream at a temperature for example, from 350° to 700°C for 2 to 30 hours at a hydrogen hourly feed rate of about 100 to 1000 times the catalyst volume. The last operation is preferably conducted in the hydrodealkylation reactor. It is also possible to omit the roasting step and to proceed directly to the reduction.

For the reduction step, the use of hydrogen is not absolutely necessary since we can use other reducing agents such, for example, as: hydrazine, carbon monoxide, alkyl metals (aluminum, zinc, etc...), the reduction being conducted as well in a gaseous medium as in a liquid medium.

The hydrodealkylation may be performed in at least one reaction zone i.e. in at least one reactor; we can use:

1. either one or more fixed bed reactors with the optional possibility of having a reactor for replacing the operating one during the regeneration of the catalyst in one of the fixed bed reactors, 2. or one or more fluid bed reactors, 3. or, and this is, in most cases, one of the best solutions, when the process is to be conducted in a continuous manner over a long period, at least one moving bed reactor;

the method, as described in the French patent No. 2 160 269, consists of circulating the charge and hydrogen through at least one reaction zone containing a catalyst, for example a granular one, said catalyst being progressively introduced at one of the two ends of the reaction zone and progressively withdrawn from the other of said ends of the reaction zone, and then to send the catalyst progressively withdrawn from the reaction zone, to a regeneration zone, the catalyst after regeneration and reduction in the presence of a hydrogen stream being progressively reintroduced at the end of the reaction zone opposite to that from which the catalyst has been withdrawn, so as to replace the catalyst withdrawn from the reaction zone, thereby maintaining a high and substantially constant activity level at each point of the reaction zone.

The withdrawing of the catalyst from the one or more moving bed reactors is carried out progressively as above stated. By "progressively" it is meant that the catalyst may be withdrawn:

either periodically, for example at a rate of one-tenth each 10 days, by withdrawing only one fraction at each time, for example from 0.5 to 15% of the total catalyst amount. However, it is also possible to withdraw this catalyst in shorter time (of the order of a minute or of a second for example), the withdrawn amount being reduced accordingly, or in a continuous manner.

The one or more moving bed reactors, as well as the regeneration zone may be placed at will, for example side by side. It may therefore be necessary, several times, to ensure the conveyance of the catalyst from a relatively low point to a relatively high point, for example from the bottom of a reaction zone to the top of the regeneration zone; this conveyance may be achieved by means of any lifting device, for example a "lift". The fluid of the lift used for conveyance of the catalyst may be any convenient gas, for example nitrogen or still for example, hydrogen and more particularly, purified hydrogen or recycle hydrogen.

The solid material which is displaced through the one or more moving bed reactors, may be a granulated catalyst containing a convenient carrier; this catalyst may be, for example, in the form of spherical balls of a diameter generally from 1 to 3 mm, preferably from 1.5 to 2 mm, although these values are not limitative. The density of the catalyst in bulk may be, for example, from 0.4 to 1, preferably from 0.5 to 0.9 and, more particularly from 0.6 to 0.8, these values being not limitative.

The regeneration of the catalyst is achieved by any known means or still according to the method described, for example, in the French patent No. 2 160 269.

When the acidity of the alumina is deemed too high (thus when a metal is introduced by means of a solution of a compound containing halogen, it remains or it may remain small halogen amounts, even after the final calcination of the catalyst, which may lower the catalyst quality), said acidity can be modified by adding before or after the introduction of the active elements, certain compounds capable of modifying the surface acidity of the solid material either by themselves or by the action of the products derived therefrom, after their decomposition on the carrier, under suitable conditions.

According to the case, we can make use of derivatives of metals from groups I A, II A and III B of the periodic classification of elements (i.e. the alkali and earth-alkali metals or such metals as scandium or yttrium) or elements which are capable by themselves to modify the acidity of the carrier while simultaneously introducing at least some, if not all, of the properties that the final catalyst must exhibit (activity, selectivity, long life time, good resistance to poisoning etc...). We will mention particularly, the elements from groups I B, II B, III A and IV B of the periodic classification of elements and, more particularly, copper, silver, gold, zinc, cadmium, gallium, indium, thallium, germanium, tin and lead.

Generally, it is not necessary to add these elements in an amount greater than 5% and, in most cases, 2% by weight with respect to the final catalyst.

The following examples given for illustrating the invention, are not limitative.

EXAMPLE 1

A catalyst according to the invention is prepared by impregnating alumina with an aqueous solution of hexachloroiridic acid, drying at 120°C for 4 hours and roasting at 500°C for 2 hours. The catalyst is then charged into a tubular reactor and reduced in a hydrogen stream at 550°C for 15 hours. The alumina carrier, before impregnation, had the following properties:

specific surface: 9.5 m$^2$/g
pore volume: 0.48 cc/g
percent of n-heptane cracked in the above-mentioned conditions: 0.8 % by weight.

The finished catalyst contains 0.4 % by weight of iridium. Its specific surface is 9 m$^2$/g, its pore volume 0.45 cc/g and its heat of neutralization by ammonia adsorption is 3 calories per gram of catalyst at 320°C under 300 mm Hg.

Over this catalyst, we pass a charge under the following conditions:

total pressure: 12 kg/cm$^2$
temperature: 550°C
V.V.H.: 4 volumes of liquid charge per volume of catalyst and per hour,
hydrogen relative flow rate: 5.7 moles per mole of hydrocarbon of the charge,
test duration: 300 hours.

The respective compositions of the charge and of the effluent from the reactor after cooling thereof and separation of hydrogen and hydrocarbon gases, are reported in table I below.

TABLE I

| Composition in moles % | Charge | Effluent |
| --- | --- | --- |
| n hexane | 0.5 | — |
| benzene | 4 | 51.0 |
| toluene | 70 | 43.5 |
| ethyl benzene | 17 | 2 |
| xylenes | 8.5 | 3.5 |
| heavy products (aromatics having more than 8 carbon atoms | — | not detectable |

Moreover, it is observed that no substantial degradation of the aromatic ring occurs, the total number of aromatic moles recovered corresponding substantially, except for the small difference due to experimental errors, to the total number of moles introduced into the reactor. The gaseous hydrocarbons, accordingly, result substantially exclusively from the dealkylation of alkyl aromatic hydrocarbons or from the cracking of paraffins already present in the charge. The benzene yield may thus be easily calculated from the data of Table I. Here it is 51.3 moles of benzene per 100 moles of aromatics in the reactor charge.

It is also noticeable that this yield was maintained with a remarkable stability over all the test duration, which was 300 hours.

It is also remarkable to observe that the formation of heavy products is not detectable and that the coke content of the catalyst was found nil.

We have compared the performances obtained with the catalyst described at the beginning of this example with those achieved by a catalyst not conforming to the invention, having the same composition, but the following properties:

specific surface: 170 m$^2$/g
pore volume: 0.60 cc/g
percent of n-C$_7$ cracked : 5.8% by weight
heat of neutralization by ammonia adsorption at 300°C under a pressure of 300 mm Hg : 18 calories/g.

This catalyst and that according to the invention have been tested under the same conditions as at the beginning of the example except the temperature which is indicated in Table I.

The benzene yields as well as the percent of the charge transformed to heavy products, are compared in Table II below:

TABLE II

| Reaction temperature °C | Yield mole % | | Catalyst of example I according to the invention: yield mole % | |
| --- | --- | --- | --- | --- |
| | Benzene | C$_9$$^+$ products | Benzene | C$_9$$^+$ |
| 550 | 42 | — | 51 | 0 |
| 570 | 48 | 0.1 | 66 | 0 |
| 590 | 47 | 0.5 | 78 | <0.1 |
| 600 | 45 | 2 | 76 | 0.1 |

It is apparent that the catalyst of the invention gives a substantially higher benzene yield as compared to that obtained with the other catalyst.

The catalyst which does not conform to the invention has a hydrodealkylating activity which is low and does not increase substantially with the temperature and gives rise to the production of increasing amounts of heavy products.

EXAMPLE 1 A (comparative)

By way of comparison, the charge of example 1 is hydrodealkylated in the presence of a conventional catalyst containing 7.5 % of chromium oxide deposited on alumina having a specific surface of 170 m$^2$/g, a pore volume of 0.60 cc/g and a heat of neutralization by ammonia adsorption of 18 calories per gram of catalyst at 320°C under 300 mm Hg.

When proceeding according to the operating conditions of example 1 (550°C, 12 kg/cm$^2$, V.V.H.: 4 and relative hydrogen flow rate of 5.7 moles per mole of hydrocarbon of the charge), we obtain, after 300 hours, a benzene yield amounting to 4 % by mole ( with a mole percent of C$_9$$^+$ which is nil).

The results are thus very poor.

When operating under the severe conventional conditions at 650°C under a pressure of 40 kg/cm$^2$, at a V.V.H. of 1 and a ratio H$_2$/H$_C$ of 5, we obtain, after 300 hours of operation, a benzene yield of 58% by mole with a mole percent of C$_9$$^+$ equal to 3.5%.

If, in these two experiments, we replace the alumina by that used in example 1, we obtain substantially the same results as in these two experiments.

EXAMPLE 1 B (comparative)

By way of comparison we use the catalyst of example 1 for hydrodealkylating the charge of example 1 under the following conventional operating conditions:
temperature: 650°C
pressure: 40 kg/cm²
V.V.H.: 4
ratio $H_2/H_C$: 5

After 300 hours, we obtain a benzene yield of 67% (by mole) but a percentage (by mole) of $C_9^+$ amounting to 1.3%.

The benzene yields are thus of the same order of magnitude as those obtained in the relatively mild conditions of example 1; on the contrary, in example 1, these milder conditions have the object of avoiding the formation of heavy products.

EXAMPLE 2

In order to illustrate the influence of the specific surface, of the pore volume and of the neutralization heat of the catalyst, we hydrodealkylate the charge of example 1 in the presence of catalysts of the same composition as in example 1 but which differ from one another by their specific surface, pore volume and neutralization heat.

The results which are reported in Table III below have been obtained at 590°C; the pressure, the V.V.H. and the ratio $H_2/H_C$ being the same as in example 1.

TABLE III

| CATALYST | | | YIELD MOLES % | |
|---|---|---|---|---|
| Specific surface (m²/g) | Pore volume (g/cc) | Heat of neutralization by ammonia adsorption at 300°C under 300 mm (calories/g) | Benzene | $C_9^+$ |
| 1 | 0.35 | 1.5 | 65 | — |
| 5 | 0.45 | 2 | 73 | — |
| 20 | 0.50 | 4.2 | 79 | — |
| 50 | 0.60 | 4 | 80 | — |
| 90 | 0.55 | 7 | 75 | — |
| 100 | 0.55 | 8 | 70 | 0.1 |
| 120 | 0.57 | 13 | 60 | 0.2 |

EXAMPLE 3

In this example, we prepare a series of catalysts deposited on the Alumina carrier described at the beginning of example 1, i.e. a carrier having a specific surface of 9.5 m²/g.

The list of the catalysts as well as their composition by weight is given below:
Catalyst A: 0.4% ruthenium
Catalyst B: 0.4% rhodium
Catalyst C: 0.4% manganese
Catalyst D: 0.4% platinum These catalysts are obtained by impregnating the alumina carrier with an aqueous solution containing: for catalyst A: ruthenium chloride, for catalyst B: rhodium chloride, for catalyst C: manganese nitrate and for catalyst D: platinum chloride. The catalyst is then dried at 120°C for 6 hours and then roasted in a dry air stream at 500°C for 2 hours.

These various catalysts are then charged into a tubular reactor, reduced at 550°C for 15 hours in a $H_2$ stream, tested in the conditions of example 1 with the charge described in example 1. The benzene yields obtained after a run of 100 hours with the various catalysts are reported in Table IV below ( The reaction temperature was 550°C).

TABLE IV

| Catalyst | A | B | C | D |
|---|---|---|---|---|
| Benzene yield (mole %) | 53 | 65 | 61 | 62 |

By way of comparison, by making use of a catalyst E containing 0.4 % of rhenium (prepared by means of an aqueous solution of ammonium perrhenate) and of a catalyst F containing 0.4 % of nickel (prepared by means of an aqueous solution of nickel nitrate), we have obtained, under the same operating conditions as above, respective benzene molar yields of 50% and 49%.

EXAMPLE 4

In this example, we have prepared a series of bimetallic catalysts on the same alumina carrier as described at the beginning of example 1, having a specific surface of 9.5 m²/g.

The list of these catalysts as well as their composition by weight is given below:

| Catalyst G : 0.2 % Ir | 0.2 % W |
|---|---|
| Catalyst H : 0.2 % Ru | 0.2 % W |
| Catalyst I : 0.2 % Rh | 0.2 % W |

The catalysts are obtained by impregnation of the alumina carrier by means of an aqueous solution containing, on the one hand, salts of Ir, Ru, Rh, such as above-described and, on the other hand, ammonium metatungstate. The solids obtained after impregnation are then treated in the same manner as the catalysts of example 1, except for the reduction step which is conducted at 580°C for 15 hours.

The results obtained after the test in the same conditions as in example 3, are reported in Table V (reaction temperature : 550°C).

TABLE V

| Catalyst | G | H | I |
|---|---|---|---|
| Benzene yield (mole %) | 55 | 57 | 68 |

EXAMPLE 5

In this example, we prepare a new series of bimetallic catalysts of the same alumina carrier as described at the beginning of example 1.

The catalysts have the following composition:

| Catalyst J : 0.2 % Ir | 0.2 % Re |
|---|---|
| Catalyst K : 0.2 % Re | 0.2 % Re |
| Catalyst L : 0.2 % Rh | 0.2 % Re |
| Catalyst M : 0.2 % Ir | 0.2 % Mo |
| Catalyst N : 0.2 % Rh | 0.2 % Mo |

The catalysts are obtained by impregnating alumina with an aqueous solution containing the precursor salts or the two metals which are to be deposited on the carrier. The Ir, Rh, Ru and Re salts are those described above and the molybdenum salt is ammonium paramolybdate. The subsequent stages of preparation and the test of the catalysts obtained are performed in the manner described in example 4 (reaction temperature: 550°C).

The results obtained are reported in Table VI below:

TABLE VI

| Catalyst | J | K | L | M | N |
|---|---|---|---|---|---|
| Benzene yield mole % | 59 | 61 | 71 | 55 | 65 |

EXAMPLE 6

In this example, we prepare another series of bimetallic catalysts with the same alumina carrier as described at the beginning of example 1.

The catalysts have the following composition:

| Catalyst O : 0.2 % Rh | 0.2 % Pt |
| Catalyst P : 0.2 % Rh | 0.2 % Ir |
| Catalyst Q : 0.2 % Rh | 0.2 % Os |
| Catalyst R : 0.2 % Os | 0.2 % Pt |
| Catalyst S : 0.2 % Os | 0.2 % Ru |
| Catalyst T : 0.2 % Os | 0.2 % Ir |
| Catalyst U : 0.2 % Rh | 0.2 % Ru |

These catalysts are obtained by impregnating the alumina with an aqueous solution containing the precursor salts of the two metals which are to be deposited on the carrier. The salts of Rh, Ir, Ru and Pt are those described above, the osmium compound is chloroosmic acid. The subsequent stages of preparation and the test of the resulting catalysts are performed in the manner described in example 4 (reaction temperature: 550°C).

The results obtained are reported in the following Table.

TABLE VII

| Catalyst | O | P | Q | R | S | T | U |
|---|---|---|---|---|---|---|---|
| Benzene yield (mole %) | 54 | 56 | 55 | 52 | 55.5 | 55 | 54 |

We claim:

1. In a process for the catalytic hydrodealkylation of alkyl aromatic hydrocarbons, conducted at a temperature from 400° to 650° C, under a pressure from 1 to 30 kg/cm² at a space velocity from 1 to 10 and a ratio of hydrogen to the hydrocarbons, expressed in mole per mole of the effluent at the outlet of the reactor, in the range from 1 to 10, wherein the improvement comprises employing a catalyst containing essentially:

a. at least one metal selected from the group consisting of ruthenium, osmium, palladium, rhodium, iridium, platinum and manganese, and
   b. an alumina, substantially inert to cracking and coking reactions in the presence of hydrogen, the metal content by weight of the catalyst being from 0.05 to 5%, the specific surface of the catalytst being from 1 to 100 m²/g., the total pore volume of the catalyst being from 0.2 to 0.8 cc/g and the heat of neutralization of the catalyst by ammonia adsorption being lower than 10 calories per gram of catalyst at 320° C under a pressure of 300 mm of Hg.

2. A process according to claim 1 wherein the alumina is gamma alumina.

3. A process according to claim 1, in which the specific surface of the catalyst is from 5 to 80 m²/g.

4. A process according to claim 3, in which the total pore volume of the catalyst is from 0.3 to 0.7 cc/g and the heat of neutralization of the catalyst by ammonia adsorption is lower than 7 calories per gram of catalyst at 320°C under a pressure of 300 mm of Hg.

5. A process according to claim 4, in which the specific surface of the catalyst is from 7 to 55 m²/g.

6. A process according to claim 5, the hydrodealkylation being conducted at 550° – 600° C.

7. A process according to claim 3, in which the specific surface of the catalyst is from 7 to 55 m²/g.

8. A process according to claim 1, in which the selected metal is used in association with at least one other metal selected from nickel, molybdenum, rhenium and tungsten.

9. A process according to claim 8, making use of a couple of metals selected from the couples: iridium-tungsten, ruthenium-tungsten, rhodium-tungsten, iridium-rhenium, ruthenium-rhenium, iridium-molybdenum, rhodium-molybdenum and rhodium-rhenium.

10. A process according to claim 1, making use of at least two metals selected from ruthenium, osmium, palladium, rhodium, iridium, platinum and manganese.

11. A process according to claim 5, making use of a couple of metals selected from the couples: rhodium-iridium, rhodium-osmium, osmium-platinum, osmium-ruthenium, osmium-iridium and rhodium-ruthenium.

* * * * *